United States Patent
Simon

(10) Patent No.: US 7,228,973 B2
(45) Date of Patent: Jun. 12, 2007

(54) NONWOVEN FIBROUS MEDIA ESPECIALLY USEFUL FOR THE SEPARATION OF BLOOD CONSTITUENTS

(75) Inventor: Larry D. Simon, Newville, PA (US)

(73) Assignee: Ahlstrom Mt. Holly Springs, LLC, Mt. Holly Springs, PA (US)

(*) Notice: Subject to any disclaimer, the term of this patent is extended or adjusted under 35 U.S.C. 154(b) by 547 days.

(21) Appl. No.: 10/444,073

(22) Filed: May 23, 2003

(65) Prior Publication Data

US 2004/0232067 A1   Nov. 25, 2004

(51) Int. Cl.
*B01D 39/02* (2006.01)

(52) U.S. Cl. .................. 210/505; 210/508; 428/137

(58) Field of Classification Search ........ 210/503–508; 55/527, 528; 428/137, 228; 604/403, 406; 162/130, 146, 149
See application file for complete search history.

(56) References Cited

U.S. PATENT DOCUMENTS

| | | | |
|---|---|---|---|
| 4,038,452 A * | 7/1977 | Kobayashi et al. ......... 442/357 |
| 4,256,693 A | 3/1981 | Kondo et al. | |
| 4,477,575 A | 10/1984 | Vogel et al. | |
| 4,512,849 A * | 4/1985 | Brandon et al. ......... 162/157.2 |
| 4,810,394 A | 3/1989 | Masuda | |
| 4,816,224 A | 3/1989 | Vogel et al. | |
| 5,186,843 A * | 2/1993 | Baumgardner et al. ..... 210/767 |
| 5,262,067 A | 11/1993 | Wilk et al. | |
| 5,454,946 A * | 10/1995 | Heagle et al. ............. 210/503 |
| 5,685,897 A * | 11/1997 | Belding et al. ............... 96/154 |
| 5,851,838 A | 12/1998 | Vetter et al. | |
| 6,660,172 B2 * | 12/2003 | Koslow ....................... 210/777 |
| 6,837,956 B2 * | 1/2005 | Cowell et al. .............. 156/252 |

OTHER PUBLICATIONS

Smook, G.A. Handbook for Pulp and Paper Technologists (1982).*
Internet Article: CFF Fibrillated Fibers-Specialty Papers d3; Engineered Fibers Technology, Brochure from EFibersTec of Shelton CT, undated, downloaded Dec. 22, 2005.*

* cited by examiner

*Primary Examiner*—Joseph Drodge
(74) *Attorney, Agent, or Firm*—Nixon & Vanderhye, P.C.

(57) ABSTRACT

Blood separation media include a non-woven web of fibrillated and non-fibrillated synthetic staple fibers. The fibrillated synthetic staple fibers will most preferably have a Canadian Standard Freeness (CSF) of less than about 300 mL, whereas the non-fibrillated synthetic staple fibers have a CSF of greater than about 700 mL. Preferably, the fibrillated synthetic staple fibers are present in an amount between about 20 to 90 wt. %, and the non-fibrillated synthetic staple fibers are present in an amount between about 10 to about 80 wt. %. The fibrillated and non-fibrillated synthetic staple fibers may be formed of the same, or different, polymeric material, such as polyesters, polypropylenes, polyethylenes, poyacrylonitriles, and polyamides. Especially preferred blood separation media will comprise a blend of fibrillated acrylic fibers, and a mixture of non-fibrillated nylon and polyester fibers, wherein the ratio of nylon and polyester fibers in the mixture thereof is between about 1:4 to about 1:2. The blood separation media of this invention can be formed by conventional "wet-laid" processes. In use, a quantity of whole blood may be brought into contact with the blood separation media for a time sufficient to separate the erythrocytes therein.

13 Claims, No Drawings

NONWOVEN FIBROUS MEDIA ESPECIALLY USEFUL FOR THE SEPARATION OF BLOOD CONSTITUENTS

FIELD OF THE INVENTION

The present invention relates generally to blood separation media. More particularly, the present invention relates to fibrous non-woven media that separates erythrocytes (commonly known as "red blood cells") from other blood constituents (e.g., serum and/or plasma) in whole blood.

BACKGROUND AND SUMMARY OF THE INVENTION

Several approaches have been used, other than centrifugation, to separate erythrocytes from whole blood to perform rapid diagnostic assays. Specifically, one prior approach, as disclosed in U.S. Pat. Nos. 4,256,693 and 4,810,394 each to Masuda (the entire content of each prior patent being expressly incorporated hereinto by reference), uses successive layers of different materials to which whole blood is applied. Each layer in the multilayer blood separation media performs a separate function. One disadvantage associated with this prior approach is that a multi-layer separation media is expensive and difficult to manufacture.

Another approach to the problem of non-centrifugal separation of erythrocytes from whole blood, as disclosed in U.S. Pat. Nos. 4,477,575 and 4,816,224 each to Vogel et al. (the entire content of each prior patent being expressly incorporated hereinto by reference), uses a layer of glass microfiber having a density of 0.1-0.5 g/cm$^3$ to separate erythrocytes from whole blood. One disadvantage to this prior approach is that papers or packings containing 100% glass microfibers are inherently weak and require extreme care in handling. Strength can be enhanced through the use of liquid binders such as acrylic or other latexes, acrylic or other synthetic resins or polyvinyl alcohol, but these binders can cause interference with the assay.

In another approach, as disclosed in U.S. Pat. No. 5,186,843 to Baumgardner et al. (the entire content of which is expressly incorporated hereinto by reference), a single-layer medium made of a composite of glass microfibers, cellulose fibers and synthetic staple fibers is used for separating erythrocytes from whole blood.

Although the blood separation media proposed in the past are suitable for their intended purpose, some improvements are still desired. For example, it would be desirable if a single layer media could be provided which performs substantially the same diagnostic functions and have substantially the same strength characteristics as compared to multilayer blood separation media. It would also especially be desirable if such a single-layer blood separation media could be formed completely of synthetic fibers. It is therefore towards fulfilling such needs that the present invention is directed.

Broadly, the present invention is embodied in blood separation media comprised of a non-woven web of fibrillated and non-fibrillated synthetic staple fibers. The fibrillated synthetic staple fibers will most preferably have a Canadian Standard Freeness (CSF) of less than about 300 mL, whereas the non-fibrillated synthetic staple fibers have a CSF of greater than about 700 mL.

In especially preferred forms, the present invention is embodied in blood separation media in which the fibrillated synthetic staple fibers are present in an amount between about 20 to 90 wt. %, and the non-fibrillated synthetic staple fibers are present in an amount between about 10 to about 80 wt. %. The fibrillated and non-fibrillated synthetic staple fibers may be formed of the same, or different, polymeric material, such as polyesters, polypropylenes, polyethylenes, poyacrylonitriles, and polyamides. Especially preferred blood separation media in accordance with the present invention will comprise a blend of fibrillated acrylic fibers, and a mixture of non-fibrillated nylon and polyester fibers, wherein the ratio of nylon and polyester fibers in the mixture thereof is between about 1:4 to about 1:2.

The blood separation media of this invention can be formed by conventional "wet-laid" processes. That is, an aqueous slurry of the fibrillated and non-fibrillated synthetic staple fibers may be formed and then subsequently dewatered to produce a non-woven web comprised of a blend of such fibrillated and non-fibrillated synthetic staple fibers.

In use, a quantity of whole blood may be brought into contact with the blood separation media for a time sufficient to separate the erythrocytes therein. More specifically, a quantity of whole blood is allowed to absorb into the blood separation media for a time sufficient to allow the plasma or serum to wick from the contact point a greater distance as compared to the erythrocytes. Such wicking, and hence erythrocyte separation, may occur radially (for example, parallel to the media surface) and/or vertically (for example, through the thickness of the media).

These aspects and advantages of the present invention will be further understood by reference to the following detailed description of a preferred exemplary embodiment thereof.

DETAILED DESCRIPTION OF THE INVENTION

A. Definitions

As used herein and in the accompanying claims, the terms below are intended to have the following definitions:

"Fiber" means a fibrous or filamentary strand of extreme or indefinite length.

"Staple fiber" means a fiber which has been cut to definite, relatively short, segments of predetermined individual lengths.

"Non-woven" means a collection of filaments and/or staple fibers in a web or mat which are randomly mechanically interlocked and/or entangled with one another.

"Synthetic fiber" and/or "man-made fiber" refers to chemically produced fiber made from fiber-forming substances including polymers synthesized from chemical compounds and modified or transformed natural polymer. Such fibers may be produced by conventional melt-spinning, solution-spinning and like filament production techniques.

"Freeness" is the measure, in mL, of the rate in which a dilute suspension of staple fiber may be drained, as described in TAPPI Canadian standard method T 227 om-94 (1994) (hereinafter sometimes referred to as "Canadian Standard Freeness" or "CSF"), the entire content of which is expressly incorporated hereinto by reference.

"Fibrils" are tiny, minute threadlike elements associated with a processed synthetic staple fiber which impart a substantially greater surface area thereto as compared to an unprocessed synthetic staple fiber.

"Fibrillated" means processed staple fibers that have been externally acted upon to form numerous fibrils and which exhibit a Canadian Standard Freeness of less than about 300 mL, preferably between about 90 to about 300 mL, more preferably between about 100 to about 250 mL, and advantageously between about 100 to about 150 mL.

"Non-fibrillated" means unprocessed staple fibers having essentially no fibrils and which exhibit a Canadian Standard Freeness of greater than about 700 mL.

"Partially fibrillated" means staple fibers that have been processed to form some amount of fibrils and which exhibit a Canadian Standard Freeness between that of fibrillated and non-fibrillated staple fibers.

"Fibrillatable" means non-fibrillated and partially fibrillated staple fibers that inherently possess the ability to be fibrillated using standard mechanical beaters, refiners and the like employed in the paper-making industry.

B. Description of Preferred Exemplary Embodiments

As noted previously, the present invention is most preferably embodied in blood separation media which includes a fibrous non-woven mass comprised of a homogenous blend or mix of fibrillated and non-fibrillated synthetic staple fibers. Most preferably, the blood separation media of this invention is in the form of a single-layer fibrous sheet (colloquially termed a "web") made from the blend of fibrillated and non-fibrillated synthetic staple fibers.

The blood separation media of the present invention necessarily comprises a homogeneously dispersed, randomly intermingled mass of fibrillated and non-fibrillated synthetic staple fibers. Most preferably, the blood separation media of the present invention is in the form of a single layer of non-woven fibers having a bulk density of less than about 0.55 g/cm$^3$, more preferably between about 0.10 to about 0.30 g/cm$^3$, and advantageously about 0.25 g/cm$^3$. The media of the present invention will advantageously have basis weights in the range of 35 g/m$^2$ to about 250 g/m$^2$. The thickness of the media according to the present invention is not critical, but will preferably be between about 0.15 to 1.10 mm, typically about 0.45 mm.

Virtually any fibrillated synthetic staple fibers may be employed in the practice of this invention, including fibers formed of polyesters, polypropylenes, polyethylenes, poyacrylonitriles (acrylics), and polyamides (nylons, for example, nylon-6, nylon 6,6, nylon-6,12, and the like). Most preferred are fibrillated staple fibers formed from acrylics. One particularly preferred form of fibrillated staple acrylic fibers is Grade CFF available commercially from Sterling Fibers, Inc. of Pace, Fla.

The fibrillated synthetic staple fibers may be formed from non-fibrillated or partially fibrillated staple fiber feedstock, provided that such fibers are fibrillatable. Thus, according to the present invention, non- or partially fibrillated synthetic staple fibers may be refined in conventional pulp beaters, refiners or like mechanical means so as to fibrillate the same to a CSF of about 90 ml or greater as noted previously.

Virtually any non-fibrillated synthetic staple fiber may be employed in the practice of the present invention, including staple fibers formed from polyesters, polypropylenes, polyethylenes, poyacrylonitriles (acrylics), and polyamides (nylons, for example, nylon-6, nylon 6,6, nylon-6,12, and the like). Preferred are polyesters and nylons, with a mixture of polyester and nylons being especially preferred.

The fiber diameters of the fibrillated and non-fibrillated synthetic staple fibers are not particularly limited. Thus, for example, a wide range of fiber diameters from about 0.5 denier to greater than 1.0 denier may be used satisfactorily in the practice of the present invention.

The blood separation media of this invention will most preferably comprise from about 20 to about 90 wt. %, more preferably from about 40 to about 80 wt. %, and most preferably from about 60 to about 70 wt. % fibrillated synthetic staple fiber. The non-fibrillated synthetic staple fiber will be present in an amount ranging from about 20 to about 80 wt. %, preferably from about 20 to about 60 wt. %, and most preferably from about 30 to about 40 wt. %.

As noted previously, if the non-fibrillated synthetic fiber component of the blood separation media according to the present invention comprises a blend of non-fibrillated nylon and polyester staple fibers, then the weight ratio of nylon to polyester fibers should be between about 1:4 to about 1:2, and more preferably about 1:3.

One especially preferred embodiment of the present invention comprises between about 60 to about 70 wt. % fibrillated acrylic staple fibers, and between about 30 to about 40 wt. % non-fibrillated synthetic staple fibers comprised of a mixture of nylon and polyester staple fibers at a weight ratio of nylon fibers to polyester fibers between about 1:4 to about 1:2.

Other additive fibers conventionally employed in blood separation media may likewise be incorporated into the media sheets of the present invention. For example, glass and/or cellulosic fibers may be incorporated into the blood separation media as may be desired. Furthermore, additives such as relatively low melt-point binder fibers, acrylic latex fibers, polyvinyl acetate fibers and the like may be employed. If used, such optional additive fibers are most preferably employed in relatively small amounts of less than about 20 wt. %, and most preferably less than about 10 wt. %. Of course, the use of any such optional additive fibers should not be such as to interfere with the blood separation function of the media.

The blood separation media may be made using conventional "wet-laid" paper-making technology. Thus, for example, predetermined amounts of selected fibrillated and non-fibrillated synthetic staple fibers (along with any optional additive staple fibers) and water may be placed in a pulper or beater. The fibers are mixed and dispersed by the pulper or beater evenly in the water to form a slurry batch. Some mechanical work can also be performed on the fibers to affect physical parameters, such as permeability, surface properties and fiber structure. The slurry batch may thereafter be transferred to a mixing chest where additional water is added and the fibers are homogenously blended. The blended slurry may then be transferred to a machine chest where one or more slurry batches can be combined, allowing for a transfer from a batch to a continuous process. Slurry consistency is defined and maintained by agitation to assure even dispersion of fibers. In this regard, the slurry may optionally be passed through a refiner to adjust physical parameters.

The slurry is then transferred to a moving wire screen where water is removed by means of gravity and suction. As water is removed, the fiber form into a paper mat having characteristics determined by a number of process variables, including for example, the slurry flow rate, machine speed, and drainage parameters. The formed sheet may optionally be compressed while still wet so as to compact the paper and/or modify its surface characteristics. The wet paper mat is then moved through a drying section comprised of heated rollers (or "cans" in art parlance) where most of the remaining entrained water is removed. Heat may also be applied to melt any binder fibers present resulting in fiber-to-fiber bonding for improved strength. The finished paper may then be taken up on a roll for further processing into finished blood separation media products.

C. EXAMPLES

The present invention will be further understood after consideration is given to the following non-limiting examples.

In the examples, a slurry of the noted fibers was first formed and then dewatered using a forming screen so as to produce wet-laid handsheets having a basis weight of about 72.0 g/m$^2$. Samples measuring 1.5 inches by 3 inches were cut from the thus formed handsheets and tested for blood separation characteristics.

Each sample was suspended across the open top of a beaker such that nothing was in contact with the bottom surface of the sample. One (1) pendant drop (approximately 50 µL) of citrated bovine blood was dropped onto the top surface of the suspended sample and the time (in seconds) needed for the sample to absorb fully the blood drop was determined. Immediately after the blood had been absorbed, the diameter (mm) of the entire liquid spot and the diameter (mm) of the red portion of the spot were measured. Proper separation was determined by the plasma forming a concentric ring around the red blood cells, and by visually observing the plasma to be clear to pale in appearance with no red streaking.

Example I

Fibrillated acrylic staple fibers identified as CFFV111-3 from Sterling Fibers, Inc. were further refined to a CSF (Canadian Standard Freeness) of 133 mL. Handsheet samples were formed as identified in Table 1 below. Specifically, handsheet samples of the fibrillated acrylic staple fibers and mixtures of non-fibrillated nylon fibers (6.0 denier×¼-inch) and polyester staple fibers (0.5 denier×⅛-inch) were made and tested for blood separation properties. The results appear in Table 1 below.

Example II

The degree of fibrillation was evaluated using acrylic staple fibers (3.3 denier×7 mm). Specifically, acrylic staple fibers were refined to cause fibrillation in the amount stated in Table 2 below using a Niagra type laboratory beater. The refined acrylic fibers in an amount of 60 wt. % were combined with 10 wt. % nylon staple fibers (6.0 denier×¼-inch) and 30 wt. % polyester staple fibers (0.1 denier×3 mm) using a British Disintegrator and then formed into wet-laid handsheets. Samples cut from the handsheets were evaluated for blood separation characteristics with the data appearing in Table 2 below.

TABLE 2

| | | | Blood Separation | | | |
|---|---|---|---|---|---|---|
| Sample No. | Refining Time (minutes) | CSF (mL) | Diameter Plasma + RBC (mm) | Diameter RBC (mm) | Blood Absorption Time (sec) | Comments |
| 12 (Comp) | 30 | 825 | 0 | 0 | N/A | nbs |
| 13 (Comp) | 90 | 775 | 0 | 0 | N/A | nbs |
| 14 (Comp) | 120 | 650 | 0 | 0 | N/A | nbs |
| 15 (Comp) | 150 | 513 | 0 | 0 | N/A | nbs |
| 16 (Comp) | 180 | 413 | 0 | 0 | N/A | nbs |
| 17 (Comp) | 210 | 338 | 0 | 0 | N/A | nbs |
| 18 (Invention) | 240 | 288 | 28 | 26 | 22.0 | plasma clear |
| 19 (Invention) | 300 | 245 | 24 | 23 | 9.3 | plasma clear |
| 20 (Invention) | 360 | 213 | 20 | 17 | 11.3 | plasma clear |

TABLE 1

| | Sample Composition | | | Blood Separation | | | |
|---|---|---|---|---|---|---|---|
| Sample No. | Fibrillated Acrylic | Nylon | Polyester | Diameter Plasma + RBC (mm) | Diameter RBC (mm) | Blood Absorption Time (sec) | Comments |
| 1 (Comparative) | 100% | — | — | 15 | 8 | >240.0 | plasma discolored |
| 2 (Invention) | 90% | 10% | — | 20 | 10 | >240.0 | plasma clear |
| 3 (Invention) | 80% | 20% | — | 24 | 13 | >240.0 | plasma clear |
| 4 (Invention) | 80% | 10% | 10% | 30 | 22 | 151.2 | plasma clear |
| 5 (Invention) | 70% | 10% | 20% | 24 | 16 | 112.7 | plasma clear |
| 6 (Invention) | 60% | 10% | 30% | 26 | 20 | 93.6 | plasma clear |
| 7 (Invention) | 50% | 10% | 40% | 24 | 21 | 28.8 | plasma clear |
| 8 (Invention) | 40% | 10% | 50% | 22 | 20 | 16.2 | plasma clear |
| 9 (Invention) | 30% | 10% | 60% | 19 | 18 | 6.6 | plasma clear |
| 10 (Invention) | 20% | 10% | 70% | 19 | 18.5 | 3.0 | plasma clear |
| 11 (Comparative) | 10% | 10% | 80% | 0 | 0 | N/A | nbs |

Notes:
(1) RBC = red blood cells
(2) nbs = no blood separation

TABLE 2-continued

| | | | Blood Separation | | | |
|---|---|---|---|---|---|---|
| Sample No. | Refining Time (minutes) | CSF (mL) | Diameter Plasma + RBC (mm) | Diameter RBC (mm) | Blood Absorption Time (sec) | Comments |
| 21 (Invention) | 450 | 200 | 31 | 25 | 35.2 | plasma clear |

Notes:
(1) nbs = no blood separation

The data above in Tables 1 and 2 demonstrate that a blend of fibrillated and non-fibrillated synthetic staple fibers allow red blood cells to be separated satisfactorily. In addition, the data show that fibrillation of the acrylic staple fibers to a Canadian Standard Freeness of less than about 300 mL is necessary for blood separation to ensue in a mixture of such fibrillated staple fibers and non-fibrillated nylon and polyester staple fibers. Moreover, an increase in the degree of freeness will translate into better blood separation properties, although the blood absorption time will increase somewhat.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A blood separation medium comprising a non-woven web comprised of fibrillated and non-fibrillated synthetic polymeric staple fibers, wherein the fibrillated staple fibers are present in the non-woven web in an amount between about 20 to about 90 wt. % sufficient to separate erythrocytes from whole blood in contact with the blood separation medium; wherein the fibrillated synthetic staple fibers have a Canadian Standard Freeness (CSF) of less than about 300 mL, and wherein the non-fibrillated synthetic staple fibers have a CSF of greater than about 700 mL.

2. The blood separation medium as in claim 1, wherein said fibrillated synthetic staple fibers have a CSF of between about 100 to about 250 mL.

3. The blood separation medium as in claim 1, wherein said fibrillated synthetic staple fibers have a CSF of between about 100 to about 150 mL.

4. The blood separation medium as claim 1, wherein said fibrillated and non-fibrillated synthetic staple fibers may be formed of the same or different polymeric material selected from the group consisting of polyesters, polypropylenes, polyethylenes, polyacrylonitriles, and polyamides; and wherein the fibrillated staple fibers.

5. The blood separation medium as in claim 1, wherein said fibrillated synthetic staple fibers are present in an amount between about 20 to about 80 wt. %.

6. The blood separation medium as in claim 1, wherein said fibrillated synthetic staple fibers are present in an amount between about 60 to about 70 wt. %.

7. The blood separation medium as in any one of claims 1, 2, 3, 4, 5 and 6, wherein said fibrillated synthetic staple fibers are fibrillated acrylic staple fibers.

8. The blood separation medium as in claim 7, wherein said non-fibrillated synthetic staple fibers are comprised of a mixture of polyester and nylon staple fibers.

9. The blood separation medium as in claim 8, wherein said mixture of non-fibrillated nylon and polyester staple fibers is present in an amount of between about 20 to about 80 wt. % at a ratio of nylon fibers to polyester fibers of between about 1:4 to about 1:2.

10. The blood separation medium as in claim 8, wherein said mixture of non-fibrillated nylon and polyester staple fibers is present in an amount of between about 30 to about 40 wt. % at a ratio of nylon fibers to polyester fibers of about 1:3.

11. The blood separation medium as in claim 1, which comprises at least one additive fiber which is selected from the group consisting of glass fibers, cellulosic fibers, binder fibers, acrylic latex fibers and polyvinyl acetate fibers.

12. The blood separation medium as in any one of claims 1, 2 and 3, having a bulk density of less than about 0.55 g/cm3, and a basis weight in the range of between about 35 to about 250 g/m2.

13. A blood separation medium comprising a non-woven web which is comprised of:

fibrillated acrylic staple fibers having a Canadian Standard Freeness (CSF) of less than about 300 mL, and non-fibrillated synthetic stable fibers having a CSF of greater than about 700 mL, wherein the non-fibrillated synthetic staple fibers are comprised of a mixture of non-fibrillated synthetic polyester staple fibers and non-fibrillated synthetic nylon staple fibers; and wherein the mixture of non-fibrillated polyester and nylon staple fibers is present in an amount of between about 20 to about 80 wt. % at a ratio of nylon staple fibers to polyester staple fibers of between about 1:4 to about 1:2.

* * * * *